United States Patent
Engel et al.

(10) Patent No.: US 6,368,621 B1
(45) Date of Patent: Apr. 9, 2002

(54) PREPARATION IN PARTICULAR FOR USE AS A MEDICATION AND/OR FOOD SUPPLEMENT

(75) Inventors: Dieter Engel, Zuzwil; Georg Kokkinis, Freidorf, both of (CH)

(73) Assignee: Peter Greither, Kirchberg (CH)

( * ) Notice: Subject to any disclaimer, the term of this patent is extended or adjusted under 35 U.S.C. 154(b) by 0 days.

(21) Appl. No.: 09/627,164

(22) Filed: Jul. 27, 2000

(30) Foreign Application Priority Data

Jul. 28, 1999 (EP) .............................. 99810681

(51) Int. Cl.⁷ ............................ A61K 9/48; A61K 9/14; A61K 47/00
(52) U.S. Cl. ..................... 424/451; 424/489; 424/439
(58) Field of Search ................................ 424/451, 489, 424/439

(56) References Cited

U.S. PATENT DOCUMENTS

| | | | | |
|---|---|---|---|---|
| 4,118,509 A | * | 10/1978 | Lattrell et al. | 424/295 |
| 4,575,502 A | * | 3/1986 | Hider et al. | 514/184 |
| 4,710,387 A | * | 12/1987 | Uiterwaal et al. | 426/72 |
| 4,976,960 A | * | 12/1990 | Grossman et al. | 424/195 |
| 5,120,763 A | * | 6/1992 | Yehuda | 514/547 |
| 5,709,888 A | * | 1/1998 | Gil et al. | 424/522 |

* cited by examiner

*Primary Examiner*—Thurman K. Page
*Assistant Examiner*—Rachel M. Bennett
(74) *Attorney, Agent, or Firm*—Nath & Associates PLLC; Gary M. Nath; Jerald L. Meyer

(57) ABSTRACT

The present invention relates to a preparation which contains at least one physiologically effective iron complex and at least one polyunsaturated fatty acid in free or chemically bonded form, in particular for use as a medication and/or food supplement. The preparation according to the invention may be preferably used for manufacturing a medication and/or food supplement for treating or the prevention of deficiency symptoms as they may occur during pregnancy and breastfeeding. Furthermore antioxidizing agents and folic acid may be contained in the preparation according to the invention.

16 Claims, No Drawings

PREPARATION IN PARTICULAR FOR USE AS A MEDICATION AND/OR FOOD SUPPLEMENT

I claim priority under 35 U.S.C. § 119 for European application Nr. 99810681.9-2114 which is hereby incorporated by reference in its entirety and for all purposes.

The invention relates to a preparation according to the preamble of claim 1, in particular for the use as a medication and/or as a food supplement.

The human body relies on the supply of a series of essential substances which it is not in the position to synthesise itself. There is a risk of an under-nourishment of these substances with an insufficient or one-sided food intake. In spite of a sufficient and balanced food intake, an undersupply of certain substances may occur under certain stress situations. Stress situations occur to the first degree with particular physical exertion, such as for example with serious sports, or also during pregnancy and breastfeeding.

Also during pregnancy and breastfeeding there are a series of substances which are necessary for the healthy development of the child and for the health of the mother. One of the most important substances from the class of vitamins has been shown to be folic acid. As medical studies show there is a clear connection between folic acid deficiency symptoms and the feared neural tube defect with newborn children, such as e.g. published by R. D. Williams, FDA Consumer, May 1994, page 11–12 and O. Tönz, Schweizer Apothekerzeitung, 1996, 17, pages 424–426.

More recent trials indicate the conclusion that a sufficient supply of polyunsaturated fatty acids in free form and/or as glycerides is likewise not to be neglected during pregnancy and breastfeeding Polyunsaturated fatty acids can belong to three different families which differ by way of the position of the first double bonding, calculated from the methyl end of the fatty acids. In medical studies ω-3-polyunsaturated fatty acids (linolenic acid family);
ω-6-polyunsaturated fatty acids (linoleic acid family) and
ω-9-fatty acids have shown to be physiologically important.

The polyunsaturated fatty acids of the ω-3 and ω-6 type are precursors for forming important tissue hormones such as e.g. prosetaglandine or leukotriene. Several independent studies render the conclusion that a higher intake of polyunsaturated fatty acids from the ω-6 and ω-3 series improves the sharpness of vision of newborn children and generally encourages the infant brain development. With this, 5,8,11,14-eicosatetranoic acid and docosahexaenoic acid as metabolites of linoleic and linolenic acids appear to play a particular role (D. Kunze, 49. DGF Annual Meeting on 01.09.1993 in Karlsruhe).

The female body by way of pregnancy is subjected to an increased oxidative stress. Oxidative stress is indicated as an increased activity of free radicals. This may either be caused by way of a higher production of free radicals or by way of the undersupply of protective anti-oxidatively acting substances. Amongst other things the increased oxidative stress in vivo is held to be responsible for the pregnancy-induced high blood pressure, as cited in S. J. Wisdom, R. Wilson, J. H. McKillop, J. J. Walker, Am. J. Obstet, Gynecol., 12/1991, page 1701–1704. In particular in pregnancy there exists the requirement for anti-oxidatively acting substances.

The term antioxidant agents is to be understood as organic compounds which inhibit or prevent the undesired changes in other substances caused by the effect of oxygen and other oxidative processes. Tocopherols, carotinoids, tocotrienols, ascorbic acids, selenium, polyphenols, flavonoides, flavones are known as radical scavengers or participate closely with the respiratory chain and thus protect the functional and structural intactness of lipids and other important substances such as blood, biomembranes and cell contents.

Iron has a particular importance with regard to minerals and trace elements. The iron requirement of mother and child is an important factor of prenatal and postnatal health on account of the build-up of special foetal haemoglobin, whose conversion after birth serves in filling the iron store in kidney and liver.

Bivalent iron salts—in the oral administering form—are to be seen as the most effective iron intake substances. The degree of iron uptake is however relatively small. In order to ensure a sufficient bio-availablity the administering of high quantities of iron salts is often necessary. High quantities of iron salts and in particular the free iron ions arising by way of dissociation leads to incompatibility reactions such as sickness, vomiting and diarrhea or constipation. Trivalent iron salts as iron suppliers are practically ineffective since in the intestines they break down into iron oxide or iron hydroxides.

A further problem which is linked to the administering of Fe(II) are lipid-peroxidation processes of unsaturated fatty acids which apart from other causes also run their course under the catalytic effect of iron (II). By way of the lipid peroxidation there arise mutagenic and carcinogenic substances such as e.g. α and β unsaturated aldehydes. However also damage to cell membranes and other cell components may be led back to these oxidisation processes.

Anti-oxidant agents act as radical scavengers with lipid peroxidation procedures and in this manner may end chain reactions. On the other hand the substances used as radical scavengers change themselves with the "neutralisation". In any event this is not desirable in the case that vitamins as essential substances are to be supplied to the body.

The auto-oxidation of unsaturated fatty acids in the presence of oxygen and catalysts plays a decisive and in its effects not desired role when fats or oils become rancid (S. Ullmann's Encyclopedia of Industrial Chemistry, Eds. L. Kandy, J. F. Rounsville, G. Schulz, $5^{th}$ ed., Vol A 10, pages 190 onwards., 1987). This process is encouraged or accelerated by the presence of metal catalysts.

In particular, free fatty acids and volatile carbonyl compounds such as e.g. aldehydes and keto-compounds arising by way of the auto-oxidation are responsible for the unpleasant accompanying taste and odour of aged fat.

The primary products formed by auto-oxidation, such as hydroperoxides, the acid number and the number of volatile carbonyl compounds, in particular the aldehydes, serve as a measurement parameter and for fixing limit values for the storage and manufacture.

The formulation of a preparation which contains a combination of polyunsaturated fatty acids in free or chemically bonded form and physiologically effective iron salts, in particular iron (II) salts, is for reasons of the reactivity of the substances and the instability of such preparations resulting therefrom burdened with great difficulties and has until now not been realised.

The object of the present invention is the avoidance of disadvantages of the state of the art.

In particular it is the object to combine physiologically effective iron-containing compounds with unsaturated fatty acids in a free or chemically bonded form into a preparation without there occuring a considerable reduction of the physiological effectiveness of one or both components. The combination should be possible without preceding complicated protective steps such as e.g. a micro-encapsulation of individual or of all components.

A further object lies in the preparation of a storage-stable, multi-component preparation which apart from physiologically effective iron-containing compounds and unsaturated fatty acids in free and/or chemically bonded form further contains physiologically effective components, and in particular is used for manufacturing a medication and/or a food supplement for the prevention and treatment of deficiencies.

These objects are achieved by the characterising features of patent claim 1.

In particular they are achieved by a preparation which contains at least one physiologically effective iron complex and at least one unsaturated fatty acid in free and/or chemically bonded form.

"Physiologically effective" is to be understood in that the iron complex on the one hand does not create any or only insignificant undesired side effects in the human body and on the other hand is in the position of preventing or treating and relieving iron deficiency.

The preparation according to the invention may preferably be used as a medication and/or as a food supplement.

In the broadest sense the term "complex" is to be understood as a compound of a higher order which formally arises by the stochiometric combination of molecules and/or ions capable of existing individually or independently of one another. This is to be understood in contrast to the compounds of first order in for creation of which atoms are involved. In the course of formation of complexes several uncharged or charged (one or more) groups L (ligands) are added to an uncharged or charged atom Z (the central atom or ion) according to its coordination number n. Iron as a transition metal bonds such ligands which have free or $\pi$-electron pairs at their disposal and which may interact with the vacant hybrid orbitals of the iron for forming a complex.

In a preferred embodiment the ligands are at least bidentate, i.e. ligand or ligands with at least two complex-forming atoms may add a central atom and form the so-called chelate compounds. As a rule the complex-forming atoms are O, S and N. Complexes with bidentate and multidentate chelate ligands are more stable than complexes with non-bridged ligands.

Since the physiologically effective iron complexes are acting in the body in competition with other complex formers, such as they are made available by the diet (proteins, peptides, polycarbon acids, sugars, phosphates, thiols and other potential ligands in the intestinal tract), the complex stability must be so large that the iron complex applied is not essentially subjected to competition reactions with "competitive" complex formers. The stability must however be smaller than that of the mucosal transferin so that the iron may be taken over at the acceptor locations of the transfer system. The complex stability must preferably be so large that the occurence of free iron ions in water and preferably also under pH conditions as they are in the stomach or intestinal tract essentially does not take place. The iron complexes used in the preparation according to the invention may however have a certain water solubility.

Iron complexes which fullfill the above mentioned conditions and are applied for treating iron deficiency are known. It has now been surprisingly ascertained that at least one of these iron complexes and at least one poly-unsaturated fatty acid in free or chemically bonded form can be combined in a preparation without there occuring any significant changes under standard conditions within 6 months, e.g. by oxidation and hydolysis processes of the unsaturated fatty acids.

The preparation according to the invention should not exceed peroxide numbers (UOP) of 10 (meq $O_2$/kg), preferably the UOP lies at a highest value of 5 meq $O_2$/kg and even more preferred with maximum values of 3 meq $O_2$/kg (method 7/5.2 according to the "Schweizer Lebensmittelbuch, July 1994). Furthermore the evaluation of the aldehydes and free fatty acids serves as a measuring parameter.

As standard conditions there are defined a temperature of 25° C. ±2° C., a relative air humidity of 60% +5% and a pressure of 1 bar.

In a preferred embodiment of the present invention the iron has a oxidation step of +III in the iron complex. A further preferred embodiment form is the iron in the oxidation step ±0 in the iron complex.

The use of complexes which contain iron in the oxidation step +II and which correspond to the mentioned conditions may likewise be applied in the preparation according to the invention either solely or in combination.

For the preparation of the present invention physiologically effective iron(III) complexes are suitable with the precondition that they fullfill the already mentioned conditions.

Preferably the 3-hydroxy-4-pyrone iron complexes and derivatives thereof described in EP 107 458 are applied. The derivatives comprise those 3-hydroxy-4-pyrone iron complexes in which one or more of the hydrogen atoms of the pyrone ring is replaced by an aliphatic carbon chain. Preferably the carbon chain contains one to six carbon atoms. In a preferred embodiment the derivative of 3-hydroxy-4-pyrone is maltol (3-hydroxy-2-methyl-4-pyrone).

The 3-hydroxypyrid-2-on iron complexes and derivatives of this described in EP 0 094 149 are further used in the preparation according to the invention.

Iron(III)-hydroxide-polymaltose complexes, as are described in the "Deutsche Apotheker Zeitung", 121 Year, No. 41, page 2193 to 2195 by H. Jakobs have also been shown to be suitable according to the invention.

As iron complexes which have iron in the oxidation step 0, iron pentacarbonyl complexes (iron-ferronyl according to Food Chemical Codex, $4^{th}$ ed., 1999) and ferrocene have been shown to be particular suitable.

The preferred Fe(III) 3-hydroxy-4-pyrone-complexes, as well as Fe(III) 3-hydroxy-4-pyrid-2-one complexes and their derivatives, in particular maltol may be present in the neutral form and thus at a ratio of ligand : Fe(+III) of 3:1. But also iron(III) complexes which have molar ratios of the ligands : iron of 2:1 and 1:1 may be applied according to the invention and in the course of the present invention fall under the description of the neutral form. These ratios however render necessary the presence of further anions such as chloride in order to compensate the charging of the central atom.

The Fe(III) content may according to the complex also vary within the same type of complex. As a daily iron intake of an adult generally a quantity between 2 to 4 mg or iron is seen as sufficient. The quantity of the iron complex used in the preparation according to the invention should accordingly be present such that iron is present in the preparation between 0.1 to 20 mg, preferably in a region of 5 to 18 mg and even more preferred in a region of 10 to 15 mg, in order to alleviate iron deficiency. These values relate to a single daily intake of a suitable administering form.

Apart from the iron(III)-hydroxypyron, iron(III)-hydroxypyridon and iron(III)-hydroxide-polymaltose complexes which may be applied either alone or in combination with one another, further Fe(III) complexes such as iron(III)-citrate complexes may likewise be applied alone or in mixtures with the previously mentioned complexes in the preparation according to the invention.

A further factor which plays a role with the bioavailability of iron is the ability of the iron complexes to penetrate biological membranes. One of the possible indicators for this membrane permeation is $K_{part}$. $K_{part}$ describes the ratio between the concentration of the compound in n-octanol to the concentration of the compound in the aqueous phase. Although the iron complex as well as its corresponding metal-free compound should be able to enter through the biomembrane, both should also have a certain degree of water solubility. In the course of the present invention the iron complexes preferably have $K_{part}$ values in a region between 0.02 and 6.0, preferred between 0.1 and 4.0 and even more preferred between 0.2 and 1.0. The metal-free complex preferably has $K_{part}$ values between 0.05 and 3.0, preferred between 0.1 and 2.0 and even more preferred between 0.2 and 1.0.

In a preferred embodiment form the unsaturated fatty acids used in the preparation according to the invention in free or chemically bonded form are selected from the group consisting of $\omega$-3 and $\omega$-6 polyunsaturated fatty acids.

The term "chemically bonded" should stand for all the unsaturated fatty acids which are present other than as a free form, e.g. in the form of their glycerides (monoglyceride, diglyceride or triglyceride) in oils, fats or other types of esters. They are used alone or in mixtures with one another.

Preferably they are, in the form in which they occur with their extraction, combined with the remaining components in the preparation according to the invention, so that e.g. docosahexaenoic acid and eicosatetraenoic acid are present in concentration and structure as e.g. in fish oils. They may however also be purified, highly enriched and when required re-estered as glycerides or fatty acids.

Preferably the $\omega$-3 polyunsaturated fatty acids belong to the linolenic acid family, whilst the $\omega$-6 polyunsaturated fatty acid preferably come from the linoleic acid family.

The $\omega$-3 and the $\omega$-6 polyunsaturated fatty acids are preferably applied in a quantity of 5 to 75% by weight with respect to the total weight of the preparation, preferably in a quantity of 30 to 70% by weight and even more preferred in a quantity of 50 to 60% by weight. These quantities may be obtained from one of the fatty acids alone or from mixtures of both.

For most of the substances which may be applied in the preparation according to the invention a quantity specification is preferred which is directed towards the RDA (recommended daily allowance) values. The quantity of acids from the linolenic and linoleic acid family, in particular of $\omega$-3 and $\omega$-6 fatty acids lies between 30 mg and 100 mg (100% free fatty acid) per administering form with a single daily intake, preferred between 50 mg and 800 mg and even more preferred between 80 and 250 mg.

In a preferred embodiment form the $\omega$-3 unsaturated fatty acid is docosahexaenoic acid (C-22: ($\omega$-3) and/or eicosapentaenoic acid and/or eicosatetraenoic acid. Docosahexaenoic acid and eicosapentaenoic acid occur as a mixture in particular in fish oils.

In a further preferred embodiment form the unsaturated fatty acids of the linolenic and linoleic acid family are of a vegetable origin and are contained in fatty oils as e.g. are extracted from borage or evening primrose.

Particularly advantageous in the preparation according to the invention fat-soluble and water-soluble radical scavengers from the group of tocopherols, carotinoids, tocotrienols, polyphenols, flavonoides, flavones and ascorbate as well as additional water and/or fat soluble vitamins are applied.

As antioxidants from the group of water-soluble substances preferably ascorbic acids, flavonoides and flavones are applied in the preparation according to the invention. For reasons of stability ascorbic acid however may not be applied in a combination with iron ferronyl.

As antioxidants from the group of fat-soluble substances preferably the carotenoides (carotene, lutein, lycopin, zeaxanthin, etc.) and tocotrienols are applied. Fat-soluble vitamins with a radical scavenger function in particular are tocopherols from the vitamin E group to which also there are counted the esters of $\alpha$, $\beta$, $\gamma$, $\delta$-tocopherols.

With a single daily administering of the preparation according to the invention the administering form for adults should contain a quantity of carotenoids (>60% $\beta$-form) and polyhydroxy phenols such as flavonoids, flavones, etc.) between 4 and 25 mg, preferably from 6 to 15 mg. The quantities of vitamins is directed towards the RDA values (adults between 25 and 50 years) and for a single daily intake per administering form for adults the ranges for vitamin C lies between 20 mg and 100 mg, for vitamin E between 10 and 25 mg.

In a further preferred embodiment form the preparation according to the invention additionally contains folic acid in a quantity per administering form with a single daily intake in a range of 0.1 g to 0.6 g (87.8% purity) preferably in a quantity of 0.2 g to 0.5 g and even more preferred from 0.25 to 0.4 g.

Folic acid simplifies the treatment of anaemia which leads back to iron deficiency and furthermore, as already described, is used for the prevention of neuron tube defects.

Furthermore to the preparation according to the invention there may also be applied a zinc source in a quantity per administering form (single daily intake) of 0.5 to 20 mg, preferably from 5 to 17 mg and even more preferred from 12 to 15 mg.

In particular the preparation according to the invention may be used for manufacturing a medication and/or food supplement for treating and preventing deficiency symtoms.

Particularly a combination of folic acid, anti-oxidant agents, in particular anti-oxidatively acting vitamins, physiologically effective iron complexes and unsaturated fatty acids in a free and/or chemically bonded form, in particular with fatty acids of the $\omega$-3 and or $\omega$-6 type have been shown to be advantageous in pregnancy and breastfeeding. In particular by way of the iron complex although the iron intake is ensured, undesired side and catalytic effects of the iron are however prevented. This firstly is to be led back to the low concentration of free iron ions since the iron quantities released from the complex are directly taken up by the body. The concentration of free iron ions thus in the preparation as well as in the body lie below that quantity which to a significant degree causes undesired changes of bodily or other compounds.

The preparation according to the invention can be comprised in administering form which contains the preparation in quantities which are sufficient for a single daily intake. The required daily quantities of the physiologically effective substances in the preparation according to the invention may however also be distributed into two or more administering forms over the day. Suitable as an administering form are capsules (hard capsules (secured by stamp and sealed) and soft capsules), drink solutions and syrup. The encapsulation in e.g. soft gelatine, hard gelatine and starch capsules has been shown to be particularly suitable.

The encapsulation is effected in a closed system in nitrogen under largely water-free conditions after a heavy drying of the individual content substances.

Depending on the administering form various auxiliary substances and substrates are applied. There are applied e.g. bees wax as water protection and for increasing the viscosity, monoglycerides and diglycerides of edible fatty acids as emulsifiers, sorbitol/manitol as non-diffusing softeners (if in the administering form of a capsule), aromas for rendering inert the smell and taste of e.g. fish oil.

Soft gelatine and starch capsules which encapsulate the preparation according to the invention are preferably manufactured with the rotary die procedure.

The administering forms, in particular in the embodiment form as a capsule may have coatings resistant to gastric juice in order (where appropriate according to the composition of the preparation) to achieve a delayed release (in the intestine). Also the cross-linking of the gelatine or derivates of starch in the casing may create certain retard effects according to the composition of the preparation.

The invention is further explained by way of examples. Determining the $K_{part}$ value:

Determined is the distribution in each case for the iron complex as well as for the corresponding metal-free compound between n-octanol and aqueous tris hydrochloride (20 mM, pH 7.4; tris: 2 amino-2-hydroxymethylpropane-1,3-diol). The concentration of the substances in the respective phase is measured at 20° C. by way of spectrophotometry. 5 ml of a $10^{-4}$M aqueous solution of iron complex and metal-free compound are mixed with 5 ml of n-octanol for one minute. The aqueous n-octanol mixture arising with this is centrifuged at 1,000 G for 30 seconds. The two resulting phases are separated from one another for evaluating the concentration. The metal-free compound is measured in a region of 220 to 340 nanometers whilst for evaluating the concentration of the corresponding iron complex a region between 340 and 640 nanometers is selected. These regions also apply to the 3:1 maltol-iron(III)-complex.

The subsequent tables shows $K_{part}$ values of a few selected complexes.

| compound | distribution coefficient $K_{part}$ | |
|---|---|---|
| | metal-free compound | iron complex $[Fe^{III}$-(compound)$_3]$ |
| 3-hydroxy-1-methylpyride-2-one | 0.44 | 0.10 |
| 1-ethyl-3-hydroxypyri-2-one | 0.52 | 1.06 |
| 3-hydroxy-2-methyl-1-propyl-pyride-4-one | 0.67 | 0.53 |
| 3-hydroxy-2-methyl-4 pyrone | 0.66 | 0.5 |
| $Fe^{III}$ - EDTA | 0.001 | 0.0015 |

EXAMPLE 1

| Pregnancy preparation | |
|---|---|
| fish oil (triglyceride form) with 10% eicosapentaenoic acid (EPA) not less than 33% docosahexaenoic acid (DHA) (corresponding to >50 mg EPA, >150 mg DHA per dose) | 500 mg |
| iron (III)-hydroxide polymaltose complex with >28% Fe, (corresponding to a 18 mg Fe/dose) | 65 m |
| folic acid Ph. Eur (chemically pure folic acid >87.8%) | 0.57 mg |
| D-α-tocopherol concentrates from soya oil fractions corresponding to 36IU in the form of 2R, 4'R, 8'R-α tocopherol (24.1 mg) | 37.8 mg |
| Mono-di-glyceride of stearic acid | 50.0 mg |

EXAMPLE 2
(suitable during the last phase of pregnancy and breastfeeding)

| | |
|---|---|
| borage oil (fatty oil from seeds of Borageo officnalis) with 18–25% gamma-linolenic acid (C18:3 ω6) (corr. >90 mg GLA) | 500 mg |
| D-α-tocopherol concentrates from soya oil fractions corresponding to 12 IU in the form of 2R, 4'R, 8'R-α-tocopherol (8.05 mg) | 12.6 mg |
| iron ferronyl (FCC[1]) corr. 15 mg Fe (= approx. 1RDA[2]) | 15.03 mg |
| All-trans-β carotin, 30% suspension in vegetable oil, corr. beta-carotin 6 mg | 21.0 mg |
| folic acid Ph. Eur (chemically pure folic acid >87.8%) | 0.57 mg |
| mono-di-glyceride of stearic and oleic acid | 50.0 mg |

In a soft gelatine or starch capsule consisting of gelatine, glycerine, sorbitol, titanium dioxide, iron oxide, water
[1]FCC=food chemical Codex 4th ed. 1999
[2]RDA=recommended daily intake

EXAMPLE 3

| | |
|---|---|
| fish oil (triglyceride form) with 18% eicosapentaenoic acid and at least 12% docosahexaenoic acid (corresponding to >63 mg eicosapentaenoic acid, 42 mg docosahexaenoic acid per dose) | 350 mg |
| evening primrose oil (fatty oil from the seeds of Oenothera biennis) with 10% gamma-linolenic acid (C18:3 omega 6) | 500 mg |
| folic acid Ph. Eur (chemically pure folic acid >87.8%) (0.2) | 0.29 mg |
| iron (III) polysaccharate Ph. Helv. VII[3] (2.8–3.0% Fe) corr. 5 mg Fe (III) | 167.0 mg |
| DL-α-tocopherylacetate Ph. Eur. (corr 10 IU) | 10.5 mg |
| 30% carotene concentrate from palm fruit (biocon, Co. Quest) (thereof approx. 57% β-carotene, 32% α-carotene 11% γ-carotene, lycopin, etc, ratio cis/trans 40/60) | 10.0 mg |
| ascorbic acid Ph. Eur. (corr. 30 mg) | 33.0 mg |
| vegetable fat partly hydrated | 18.0 mg |
| bees wax yellow Ph. Eur | 24.0 mg |

In a soft gelatine or starch capsule consisting of gelatine, glycerine, sorbitol, titanium dioxide, iron oxide, water.
[3]Ph. Helv. VII=Pharmacopoeia Helvetica 7th edition.

What is claimed is:

1. A nutritional supplement preparation for pregnant and breast-feeding women, consisting essentially of:
   folic acid;
   at least one physiologically effective iron (III) complex; and
   a mixture of poly unsaturated fatty acids.

2. A preparation according to claim 1, wherein the iron complex has K part values in a range of from 0.02 to 6.0 and the corresponding metal-free compound has K part values in a range from 0.05 to 3.0.

3. A preparation according to claim 1, wherein the iron complex is selected from the group consisting of iron chelate complexes.

4. A preparation according to claim 1, wherein the iron complex is selected from the group consisting of iron (III) maltol, iron (III) hydroxide polymaltose, 3-hydroxy-4-pyrone iron complexes and derivatives thereof and 3-hydroxypyrid-2-one and derivatives thereof.

5. A preparation according to claim 1, wherein the unsaturated fatty acid is present in a quantity range of 30 mg to 1000 mg with respect to 100% free pure fatty acid per administering form with a single daily intake, preferred in a quantity range of from 50 mg to 800 mg and even more preferred in a quantity of 80 mg to 250 mg.

6. A preparation according to claims 1, wherein the preparation contains at least one anti-oxidising agent.

7. A preparation according to claim 6, wherein said antioxidising agent is selected from the group of water-soluble and/or fat soluble vitamins.

8. A preparation according to claim 7, wherein the fat-soluble vitamin is selected from the group consisting of tocopherols, carotinoids, tocotrienols, polyphenols, flavonides, flavonols and flavones preferably in a quantity of 4 mg to 25 mg per administering form with a single daily intake.

9. A preparation according to claim 8, wherein the tocopherols are selected from the vitamin E group, preferably in a quantity of up to 25 mg per administering form with a single daily intake.

10. A preparation according to claim 7, wherein the watersoluble vitamin contains ascorbic acid, preferably in a quantity of 20 mg to 100 mg per administering form with a single daily intake.

11. A preparation according to claims claim 1, wherein the preparation contains folic acid in a quantity from about 0.1 g to 0.6 g with about 87.8% purity of the folic acid per administering form with a single daily intake.

12. A preparation according to claim 1 , wherein the preparation is contained in a capsule.

13. The preparation of claim 1, wherein the mixture of polyunsaturated fatty acids is derived from fish oils.

14. The preparation of claim 1, wherein the polyunsaturated fatty acid of said mixture is selected from the group consisting of docosahexaenoic acid and eicosapentaeonic acid.

15. The preparation of claim 1, wherein the mixture contains:

polyunsaturated fatty acids derived from fish oil, about 10% eicosapentaenoic acid, and not less than about 33% docosahaxaenoic acid;

the physiologically effective iron complex is iron (III)-hydroxide polymaltose complex with greater than from about 28% Fe; and the folic acid is greater than from about 87.8% pure.

16. The preparation of claim 1, wherein the mixture contains:

polyunsaturated fatty acids derived from fish oil, about 18% eicosapentaenoic acid, not less than about 12% docosahaxaenoic acid, and evening primrose oil with about 10% gamma-linolenic acid;

the physiologically effective iron complex is iron (III)-polysaccharate from about greater than 2.8 to 3.0% Fe; and the folic acid is from about greater than 87.8% pure.

* * * * *